United States Patent
Lock et al.

(10) Patent No.: US 8,778,271 B2
(45) Date of Patent: Jul. 15, 2014

(54) DETECTION OF PEROXIDE RADICALS AND REACTION INITIATORS

(75) Inventors: John Lock, Wakefield, MA (US); Edward Geraghty, Tyngsborough, MA (US); Lawino Kagumba, Cambridge, MA (US); Norm Rice, Andover, MA (US); Keith Higginson, Leominster, MA (US); Ken Mahmud, Sudbury, MA (US); Arthur Gavrin, Litchfield, NH (US)

(73) Assignee: Triton Systems Inc., Chelmsford, MA (US)

( * ) Notice: Subject to any disclaimer, the term of this patent is extended or adjusted under 35 U.S.C. 154(b) by 338 days.

(21) Appl. No.: 12/470,201

(22) Filed: May 21, 2009

(65) Prior Publication Data

US 2009/0317913 A1    Dec. 24, 2009

Related U.S. Application Data

(60) Provisional application No. 61/054,919, filed on May 21, 2008.

(51) Int. Cl.
  *G01N 27/22* (2006.01)
  *G01N 27/04* (2006.01)

(52) U.S. Cl.
  CPC ............. *G01N 27/22* (2013.01); *G01N 27/04* (2013.01); *G01N 2291/0251* (2013.01)
  USPC .................. 422/82.02; 422/82.01; 422/82.12; 422/98; 436/135; 436/149

(58) Field of Classification Search
  None
  See application file for complete search history.

(56) References Cited

U.S. PATENT DOCUMENTS

| | | | |
|---|---|---|---|
| 4,608,333 A | 8/1986 | Ohbayashi et al. | |
| 5,045,397 A * | 9/1991 | Jensen .......................... | 428/429 |
| 6,118,124 A | 9/2000 | Thundat et al. | |
| 6,575,020 B1 | 6/2003 | de Charmoy Grey et al. | |
| 2003/0044618 A1 | 3/2003 | Fan et al. | |
| 2006/0052547 A1 | 3/2006 | Jethmalani et al. | |
| 2007/0104860 A1 | 5/2007 | Gleason et al. | |
| 2007/0278420 A1 | 12/2007 | Molhave | |
| 2008/0102532 A1 | 5/2008 | Deevi et al. | |
| 2008/0206103 A1 | 8/2008 | Pinnaduwage et al. | |

FOREIGN PATENT DOCUMENTS

WO    WO 2004/059306 A1    7/2004

OTHER PUBLICATIONS

Payne, J. A.; et al. "The Effects of Processing Variables on Stress Development in Ultraviolet-Cured Coatings," Journal of Applied Polymer Science 1997, 66, 1267-1277.*

McIntire, T. M. et al. "Unusual aggregates from the oxidation of alkene self-assembled monolayers: a previously unrecognized mechanism for SAM ozonolysis?" Phys . Chem. Chem. 2005, 7, 3605-3609.*

(Continued)

*Primary Examiner* — Yelena G Gakh
*Assistant Examiner* — Michelle Adams
(74) *Attorney, Agent, or Firm* — Pepper Hamilton LLP

(57) ABSTRACT

Sensors for the detection of free radicals and free radical forming compounds including, for example, peroxides, as well as energetic radiation, UV light, plasma or heat each such sensor including a functional component are described herein. In addition, this disclosure includes methods for making such sensors and methods for using sensors including a functional component and devices incorporating such sensors.

21 Claims, 12 Drawing Sheets

(56) References Cited

OTHER PUBLICATIONS

Johansson, SU-8 Cantilever Sensor With Integrated Readout, Ph.D. Thesis, Department of Micro and Nanotechnology, Technical University of Denmark, Oct. 1, 2006.
Tenhaeff et al., Initiated and Oxidative Chemical Vapor Deposition of Polymeric Thin Films: iCVD and oCVD, 2008, Adv. Funct. Mater. 18(7):979-992.
Love et al., Self-Assembled Monolayers of Thiolates on Metals as a Form of Nanotechnology, Mar. 25, 2005, Chem. Rev. 105(4):1103-1169.
Goeders et al., Microcantilevers: Sensing Chemical Interactions Via Mechanical Motion, Jan. 30, 2008, Chem. Rev. 108(2):522-542.
Moore, Instrumentation for Trace Detection of High Explosives, Aug. 2004, Review of Scientific Instruments 75(8):2499-2512.
Pinnaduwage et al., Detection of 2,4-Dinitrotoluene Using Microcantilever Sensors, 2004, Sensors and Activators B 99:223-229.
Applying Silanes, Gelest, Inc., 2006, www.gelest.com.
Zhou et al., Communications to the Editor, 1987, Macromolecules 20(1):233-234.
Pugh et al., Synthesis of Side-Chain Liquid Crystal Polymers by Living Ring-Opening Metathesis Polymerization. 3. Influence of Molecular Weight, Interconnecting Unit, and Substituent on the Mesomorphic Behavior of Polymers with Laterally Attached Mesogens, Jul. 6, 1992, Macromolecues 25(24):6593-6604.
Fu et al., The Synthesis of Liquid Crystalline Polymer on Gold Nanoparticles, 2001, Materials Research Society Symposium, vol. 661, pp. KK8.7.1-KK8.7.6.
Lee et al., In-Plane Enyne Metathesis and Subsequent Diels-Alder Reactions on Self-Assembled Monolayers, Sep. 23, 2005, Langmuir 21(23):10311-10315.
Mullen et al., Laser Photoionization of Triacetone Triperoxide (TATP) by Femtosecond and Nanosecond Laser Pulses, 2006, Int'l. J. Mass Spectrometry 252:69-72.
Todd et al., Application of Mid-Infrared Cavity-Ringdown Spectroscopy to Trace Explosives Vapor Detection Using a Broadly Tunable (6-8 µm) Optical Parametric Oscillator, 2002, Appl. Phys. B, Laser and Optics 75:367-376.
Ron et al., Alkanethiol Monolayers on Preoxidized Gold. Encapsulation of Gold Oxide Under an Organic Monolayer, Aug. 1, 1994, Langmuir 10(12):4566-4573.
Ron et al., Self-Assembled Monolayers on Oxidized Metals. 2. Gold Surface Oxidative Pretreatment, Monolayer Properties, and Depression Formation, Feb. 13, 1998, Langmuir 14(5):1116-1121.
Lee et al., Reactivity of Vinyl-Terminated Self-Assembled Monolayers on Gold: Olefin Cross-Metathesis Reactions, Sep. 3, 2003, Langmuir 19(20):8141-8143.
Wilson et al., Application of Selected-Ion Flow Tube Mass Spectrometry to the Real-Time Detection of Triacetone Triperoxide, Dec. 3, 2005, Analytical Chemistry 78(2):575-579.
Peanasky et al., Surface-Confined Monomers on Electrode Surfaces. 4. Electrochemical and Spectroscopic Characterization of Undec-10-ene-1-thiol Self-Assembled Monolayers on Au, Jan. 6, 1998, Langmuir 14(1):113-123.
Schulte-Ladbeck et al., Trace Analysis of Peroxide-Based Explosives, Jan. 15, 2003, Analytical Chemistry 75(4):731-735.
Pinnaduwage et al., Sensitive Detection of Plastic Explosives with Self-Assembled Monolayer-Coated Microcantilevers, Aug. 18, 2003, Appl. Phys. Lett. 83(7):1471-1473.
Yan et al., Microcantilevers Modified by Horseradish Peroxidase Intercalated Nano-Assembly for Hydrogen Peroxide Detection, Feb. 2006, Analytical Sciences 22:205-208.
Lau et al., Initiated Chemical Vapor Deposition (iCVD) of Poly(alkyl acrylates): A Kinetic Model, Apr. 11, 2006, Macromolecules 39(10):3695-3703.

\* cited by examiner

DETECTION OF PEROXIDE RADICALS AND REACTION INITIATORS

This invention was made during work supported in part by National Science Foundation Small Business Innovation Research (SBIR) Phase I Award, Contract No. IIP-0712223.

CROSS-REFERENCE TO RELATED APPLICATIONS

This application claims priority under 35 U.S.C. §119(e) to U.S. Provisional Patent Application Ser. No. 61/054,919, filed May 21, 2008, the disclosure of which is incorporated by reference in its entirety.

BACKGROUND OF THE INVENTION

1. Field of the Invention

The invention presented herein relates generally to sensors for detecting radicals, energetic radiation, plasma or heat. More specifically, the present invention relates to sensing devices for the detection of peroxide radicals and reaction initiators.

2. Description of Related Art

Microcantilever-based chemical and biological sensors can be fabricated by coating a commercially-available cantilever to enhance sensitivity and induce chemical selectivity through the choice of coating material. Depending on the choice of coating, the cantilever can be used to detect specific chemical compounds as well as proteins, DNA segments, and other biomolecules. Microcantilever chemical and biological sensors operate by responding to interactions with external stimuli in that an absorbed mass of analyte molecules causes nanomechanical bending of the microcantilever. The change in mass on the microcantilever surface due to the binding of the analyte molecules is proportional to the deflection of the microcantilever. Instead of measuring the surface stress induced due to adsorption of molecules, it is also possible to detect an added mass or an induced temperature change. Mass detection requires a resonant cantilever where the added mass is detected as a change in resonant frequency of the cantilever. Temperature changes on the surface of a cantilever can be detected by using a cantilever consisting of a sandwich of materials with different coefficients of thermal expansion. The deflection can be detected by using optical readout. The microcantilever response such as, for example, resonance frequency, phase, amplitude, Q-factor, and deflection can be simultaneously detected.

Bending and resonance response of a microcantilever are typically measured using techniques associated with atomic force microscopy (AFM). These techniques include optical reflection, piezoresistive, capacitive, and piezoelectric methods.

SUMMARY OF THE INVENTION

Embodiments of the invention are directed to a sensor for detecting reaction initiators including a functional component having a plurality of reactive groups, wherein the reactive groups exhibit a change in state of polymerization when contacted by at least one of a free radical, energetic radiation, UV light, plasma or heat, a sensing element comprising an upper surface and a lower surface, wherein at least one of the upper surface and lower surface is coated with the functional component, and at least one detector in communication with the sensing element, wherein the detector is capable of detecting the state of polymerization of the reactive groups.

In various embodiments of the invention, the sensing element comprises one or more cantilever arms capable of reacting to the state of polymerization of the reactive groups, such as, for example, by cantilever response. In certain aspects of the invention, cantilever response may be measured in bending mode. In other aspects, the cantilever response is measured in frequency mode. In some embodiments, the sensor for detecting reaction initiators further includes a substrate wherein the sensing element is fixedly attached to the substrate. The sensing element of embodiments may further comprise a base material selected from a polymer, copolymer, silicon-based compound, glass, metal, metal alloy, composite material or combinations thereof. In some embodiments, the base material is a silicon substrate. In particular embodiments, the sensor further comprises a metallic coating on at least one surface of the silicon substrate. In yet other embodiments, the sensor further comprises an adhesive layer. In still other embodiments, the sensor may further comprise a piezoresistive element for detecting a mechanical parameter associated with the one or more cantilever arms. In certain aspects, the piezoresistive element forms part of a balanced bridge, such as, for example a wheatstone bridge.

The detector of certain embodiments measures the cantilever arms reaction using piezoelectrics, optics, interferometery, capacitance, and combinations thereof. In various embodiments, the detector measures the state of polymerization by characterizing the refractive index, charge change, torsion, temperature change, surface energy change, and combinations thereof of the functional component. In some embodiments, the reaction to the state of polymerization of the reactive groups is measured as a change in resistance, a change in natural frequency or a change in the Q-mode.

In some embodiments, the functional component comprises a self-assembled monolayer. The functional component of certain embodiments comprises a head group selected from one or more of a mercapto group, an alkoxysilane having 1 to 3 oxygen atoms or a combination thereof for binding to the sensing element. In some embodiments, the head group is utilized in self assembly of the functional component. The functional component of embodiments may include a substituted or unsubstituted, branched or unbranched, alkylene or alkenylene chain of about 2 to about 20 carbon atoms. The reactive groups of embodiments may include acrylates, substituted acrylates, methacrylates, vinyls, alkenes, alkynes and derivatives and combinations thereof. In some embodiments, the state of polymerization comprises crosslinking, uncrosslinking, polymerizing or depolymerizing that is reversible, innately reversible, irreversible or regeneratably reversible.

Other embodiments of the invention are directed to a microcantilever sensor for detecting the presence of peroxide radicals including one or more microcantilevers, the microcantilevers having at least an upper and a lower surface wherein at least one said surface is coated with a functional component having a plurality of reactive groups, the reactive groups being capable of crosslinking, uncrosslinking, polymerizing or depolymerizing when contacted by at least one peroxide radical, and at least one detector in communication with the one or more microcantilevers. In some embodiments, the detector is capable of detecting a cantilever response induced by the crosslinking, uncrosslinking, polymerizing or depolymerizing of the reactive groups. In some embodiments, the detector measures the cantilever response using piezoelectrics, optics, interferometery, capacitance, and combinations thereof. The detector of embodiments may additionally measure the crosslinking, uncrosslinking, polymerizing or depolymerizing of the reactive groups by characterizing the refractive index, frequency change, charge change, torsion, temperature, surface energy and combinations thereof of the functional component.

Embodiments of the invention also provide a method for detecting free radicals including generating radicals from a sample, passing the radicals over a device having one or more sensors, the sensors comprising one or more sensing elements having at least an upper and a lower surface wherein at least one of the surfaces is coated with a functional component comprising reactive groups, said reactive groups being capable of reversible polymerization when contacted by at least one of the radicals, and detecting the polymerization of the reactive groups of the functional component. In some embodiments, the radicals are peroxide radicals, azo radicals, persulfate radicals or combinations thereof. In other embodiments of the invention a method is provided for detecting peroxide radicals including generating peroxide radicals from a sample, passing the peroxide radicals over a device comprising one or more sensors, said sensors comprising one or more sensing elements having at least an upper and a lower surface wherein at least one said surface is coated with a functional component comprising reactive groups, said reactive groups being capable of reversibly crosslinking when contacted by at least one of the peroxide radicals, and detecting crosslinking of the reactive groups of the functional component. In these methods, embodiments of the generating step may include heating the sample, irradiating the sample with light, electrochemical activation, metal ion initiation of redox reactions or combinations thereof.

In further embodiments of the invention, an apparatus for detecting the presence of peroxides is provided that includes a reactor comprising at least one chamber, at least one vapor entry opening wherein vapor enters the reactor and at least one vapor exit opening wherein vapor exits the reactor, a heat source positioned to heat vapors within the reactor, and one or more sensors. The sensors include one or more sensing elements having at least an upper and a lower surface wherein at least one surface is coated with a functional component having reactive groups, the reactive groups being capable of reversibly crosslinking when contacted by at least one free radical. In certain embodiments, the sensors may be positioned to receive the heated vapor. In certain aspects of the invention, the heat source may include an array of one or more filaments. In other aspects, the heat source may include a resistively heated element.

Embodiments of the apparatus for detecting the presence of peroxides may further include one or more detectors in communication with the one or more sensors wherein the detectors detect crosslinking of the reactive groups. In some embodiments, the apparatus for detecting the presence of peroxides further includes an apparatus for providing vapor to the vapor entry opening. In other embodiments, the apparatus also includes an alarm in communication with the detector. The vapor entry opening of certain embodiments receives ambient air. In still other embodiments, the apparatus further includes a housing surrounding the reactor where the housing is configured to provide a stand alone device, a bench top device, a handheld device or a walk-through device.

BRIEF DESCRIPTION OF THE FIGURES

For a fuller understanding of the nature and advantages of the present invention, reference should be made to the following detailed description taken in connection with the accompanying figures, in which.

DESCRIPTION OF ILLUSTRATIVE EMBODIMENTS

This invention is not limited to the particular compositions or methodologies described, as these may vary. In addition, the terminology used in the description describes particular versions or embodiments only and is not intended to limit the scope of the invention. Unless defined otherwise, all technical and scientific terms used herein have the same meanings as commonly understood by one of ordinary skill in the art. In case of conflict, the patent specification, including definitions, will prevail.

As used herein, the singular forms "a", "an" and "the" include plural reference unless the context clearly dictates otherwise.

As used herein, the term "about" means plus or minus 10% of the numerical value of the number with which it is being used. Therefore, about 50% means in the range of 45%-55%.

The terms "include", "comprise" and "have" and their conjugates, as used herein, mean "including but not necessarily limited to."

"Optional" or "optionally" may be taken to mean that the subsequently described structure, event or circumstance may or may not occur, and that the description includes instances where the event occurs and instances where it does not.

The invention described herein is generally directed to sensors for detecting radicals, energetic radiation, plasma and/or heat.

Various embodiments of the invention are directed to the detection of peroxide-containing compounds, azo-containing compounds, and persulfate-containing compounds. Such compounds may be contained within a substance (liquid, vapor, or solid), present on the surface of a substance, and/or emitted from a substance as a vapor.

Other embodiments of the invention are directed to sensors and methods for preparing sensors and methods for detecting radicals, energetic radiation, plasma and/or heat using such sensors. Further embodiments include devices and apparatuses incorporating one or more of such sensors, which can be used to monitor radicals, energetic radiation, plasma or heat or radical, energetic radiation, plasma or heat-containing or emitting substances. Such devices can be hand held, bench top or walk-through type devices. In addition, the sensors embodied herein may be incorporated into a device or apparatus for detecting one or more additional substances. For example, in some embodiments of the invention, sensors such as those described herein may be incorporated into a bomb detecting device.

Figure 1:
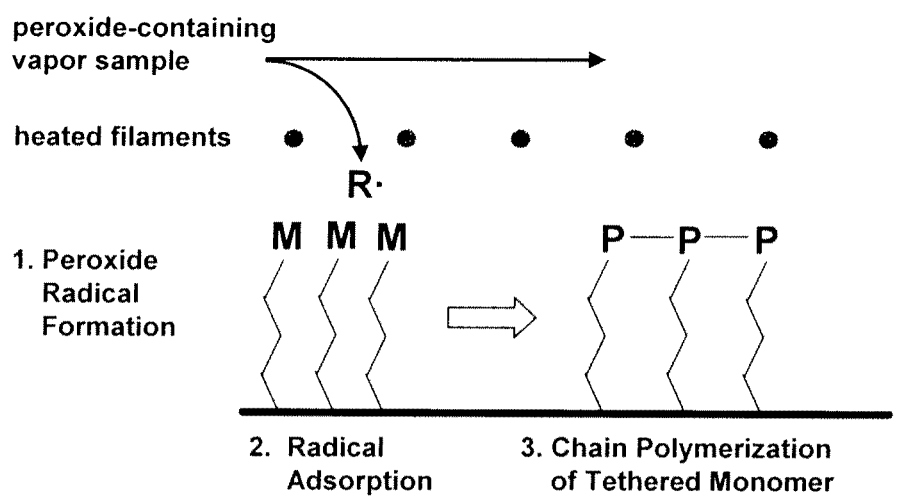
FIG. 1 is a schematic representation of sensors of one embodiment of the invention containing a functional component (M) that polymerizes (P) when contacted with a peroxide radical (R•)

The sensors of various embodiments may include one or more sensory elements that are coated on at least one side with a functional component. The term "functional component", as used herein, generally includes a material having a "head group" that facilitates binding of the functional component to the surface of the sensory element and may be fixedly attached to at least one surface of such sensory element, and a "reactive group" that interacts with radicals, energetic radiation, plasma and/or heat to facilitate crosslinking, uncrosslinking, polymerization or depolymerization of reactive groups on neighboring functional components. The functional component of sensors of various embodiments of the invention may further include "linker groups" that separate one or more head group from one or more reactive group. The linker groups may be a substituted or unsubstituted, branched or unbranched, alkylene or alkenylene chain of from, for example, about 2 to about 20 carbons. In some embodiments, the functional component may have a head group and a reactive group on opposing ends. In other embodiments, one or more reactive groups may be dispersed throughout the length of a functional component and may be separated by several linker groups. One embodiment of a functional component (M) is illustrated in FIG. 1.

Although the reactive groups of embodiments of the invention may vary, such reactive groups generally include any functional group that is capable of forming a chemical linkage or other covalent attachment to a neighboring molecule having the same reactive group or, in some embodiments, a different reactive group consistent with polymerization or crosslinking. Numerous reactive groups are known in the art and may be useful in embodiments of the invention. For example, in certain embodiments, the reactive group may be an acrylate or methacrylate-containing group. In some embodiments, the functional component may include reactive groups that are not capable of reacting with the head group. In such embodiments, the functional component may be deposited onto a surface of the sensory element without head group/reactive group crosslinking or polymerization. In other embodiments, functional components having a head group and a non-reactive "intermediate group" may be deposited onto a surface of the sensory element and the intermediate group may be later treated to transform the intermediate group into a reactive group. Embodiments of the invention also encompass sensory elements including a functional component that includes intermediate end groups. Intermediate groups may include, but are not limited to, amines, carboxylic acids and the like. Reactive and intermediate groups may be coupled to the functional component at either of the opposing ends of the functional component or in-between the head group and the terminus of the functional component.

In particular embodiments, initiation of polymerization of the reactive groups may result from interaction of such reactive groups with at least one substance such as, but not limited to, radicals, energetic radiation, plasma or heat. For example, in some embodiments, crosslinking or polymerization may be initiated by a radical derived from a peroxide or peroxide-containing substance. FIG. 1 is a schematic representation of sensors of one embodiment of the invention containing a functional component (M) that polymerizes (P) when contacted with a peroxide radical (R•). In other embodiments, the functional component may be initially crosslinked or polymerized and contact with at least one chemical substance may result in uncrosslinking or depolymerization of the reactive groups. The crosslinking, uncrosslinking, polymerization or depolymerization of functional components may be monitored to ascertain the presence of a chemical substance that mediates a change in the polymerization state of the functional component. In some embodiments, the reaction to the state of polymerization of the reactive groups is measured as a change in resistance, a change in natural frequency or a change in the Q-mode.

In still other embodiments, the functional component may further include an "initiator component." The initiator component may have a similar chemical structure as the functional component and may include a head group for mediating binding to a surface of the sensory element and a substituted or unsubstituted, branched or unbranched, alkylene or alkenylene chain of, for example, 2 to 20 carbons separating the head groups from an "initiator group" that can generate free radicals in response to, for example, ultraviolet (UV) light or heat. In some embodiments, the functional component may include a mixture of initiator groups and reactive groups. This mixture may be deposited onto the surface of a sensory element to create a functional component that is sensitive to, for example, light or heat.

Without wishing to be bound by theory, sensory elements utilizing functional components may exhibit increased sensitivity and selectivity compared to sensors that merely selectively bind or trap detected species because the initiator or the functional components embodied herein such as, for example, a free radical or peroxide radical, initiate a self amplified chemical reaction. Thus, even a minute amount of reactive peroxide may trigger a positive response making the sensors of embodiments of the invention highly sensitive and highly selective.

Figure 2A:
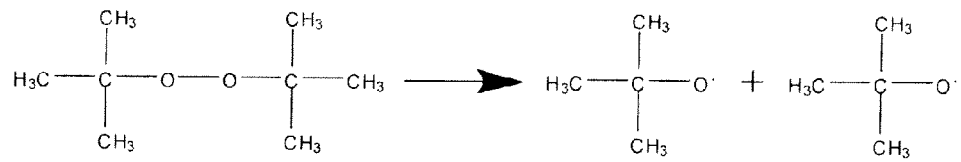
FIG. 2A illustrates free radical formation from tert-butyl peroxide.

Sensory elements including functional components may further provide increased selectivity over sensors that merely bind to or trap a detected species. For example, various embodiments of the invention are directed to the detection of peroxides by heating a sample to from about 150° C. to about 300° C. Because a peroxide contains a relatively weak O—O chemical bond, peroxide radicals can be formed from peroxide-containing substances by heating the sample to a temperature at which hemolytic cleavage of the peroxide bond occurs but other chemical bonds remain intact (e.g., about 150° C. to about 300° C.), thus avoiding the production of interfering radicals. Moreover, as illustrated in FIG. 2A, homolytic cleavage of a peroxide-containing substance (e.g., tert-butyl peroxide) results in the formation of multiple peroxide radicals, which may further increase the sensitivity and selectivity of sensors containing functional components.

Figure 2B:
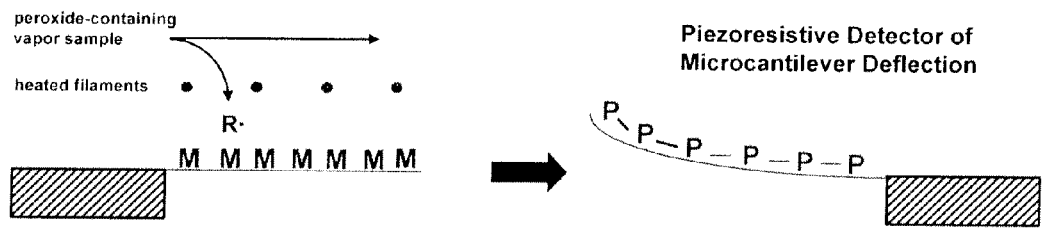
FIG. 2B is a schematic microcantilever device including a functional component (M)
Figure 2C:
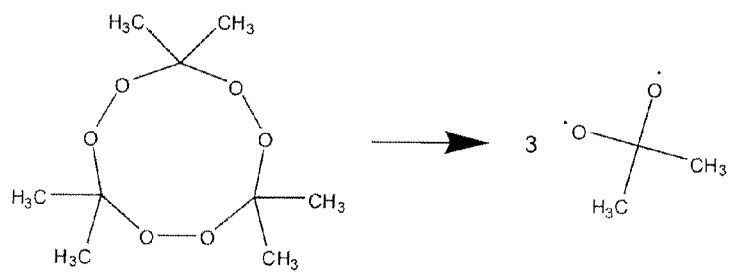
FIG. 2C illustrates free radical formation from triacetone triperoxide (TATP)
Figure 2D:
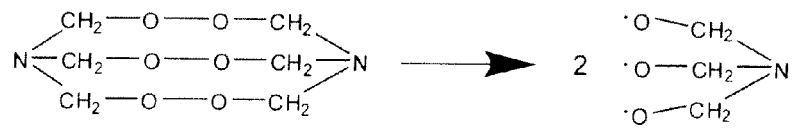
FIG. 2D shows free radical formation from hexamethylene triperoxide diamine (HMTD)

In particular embodiments, a microcantilever-based sensor, as illustrated in FIG. 2B, may be included in a device configured to detect peroxide-containing compounds utilized in explosives such as, for example, triacetone triperoxide (TATP) or hexamethylene triperoxide diamine (HMTD), or peroxides used in the manufacture of such compounds, such as, for example, hydrogen peroxide, wherein an air sample containing at least a trace amount of a volatilized peroxide is heated to from about 150° C. to about 300° C., which may initiate cleavage of each TATP or HMTD or peroxide. The generated radicals may initiate the polymerization of reactive groups of functional components deposited on the surface of the microcantilever thereby causing a cantilever response. As used herein, "cantilever response" can include, but is not limited to, deflection, rolling, torsion, change in vibrational frequency and the like of a microcantilever as a result of a change in the crosslinking or polymerization state of functional components deposited on the microcantilever. In certain aspects of the invention, cantilever response may be measured in bending mode. In other aspects, the cantilever response is measured in frequency mode. As illustrated in FIGS. 2C and 2D, heating of TATP or HMTD may result in as many as two or three separate reactive, radical-containing species, respectively, per target molecule. In such embodiments, few if any non-peroxide containing molecules would be expected to form reactive radicals, thus reducing the number of false positives. In addition, the inherent sensitivity of the microcantilever-based sensor, the multiple peroxide radicals generated from each peroxide-containing molecule, and the self-amplified nature of the polymerization response make such sensors highly selective.

In addition to a sensory element, the sensors of embodiments of the invention generally further include one or more "detector." In various embodiments, the sensory elements may be fixedly coupled to at least a portion of a substrate and the detector may be positioned to monitor the sensory element from a position wherein the detector is also coupled to the substrate or a position away from the substrate. In particular, the sensors of embodiments of the invention may also include one or more detectors positioned to detect polymerization or depolymerization of the functional component deposited on one or more surfaces of the sensory element. In some embodiments, the detector may be fixedly attached to the substrate and/or the sensory element. In other embodiments, the detector may be attached to an element not associated with the substrate or the sensory element. For example, the detector may be attached to a portion of a housing of a sensor-containing device or apparatus and positioned to monitor at least a surface of the sensory device. A variety of detectors may be used to detect polymerization or depolymerization of the functional component of the sensors of embodiments of the invention. For example, polymerization and/or depolymerization may be detected by a change in conductivity, refractive index, or surface energy, and in some embodiments, polymerization and/or depolymerization may be detected based on a change in temperature of the area surrounding the sensory element. In certain embodiments, polymerization and/or depolymerization of the functional component may be detected by a change in the shape of the sensory element. For example, in some embodiments, polymerization of the functional component may result in the deflection or twisting of the sensory element. Such structural changes of the sensory element may be monitored using various types of detectors such as, for example, optical detectors, interferometer-type detectors, piezoresistive detectors, capacitive-type detectors and the like.

The substrate of embodiments of the invention may be composed of any substance known in the art such as, for example, a polymer, copolymer, silicon, silicon nitride, glass, silica-based compound, metal, metal alloy, platinum, gold, and combinations thereof (e.g. gold-coated silicon). The sensory element of various embodiments may be fixedly coupled to at least a portion of the substrate and may be positioned on the substrate such that a sample in the form of, for example, gas, vapor, air, liquid or water, may be passed over the sensory element. For example, in some embodiments, the substrate may be a stage to which at least a portion of the sensory element is attached. In such embodiments, one surface of the sensory element may contact the substrate completely such that the surface contacting the substrate has little or no contact with the sample. In other embodiments, one or more surfaces of the sensory element may partially contact the substrate. In some embodiments, one surface of the sensory element may completely contact the substrate and one or more additional surfaces of the sensor element may partially contact the substrate. Such a configuration may allow the positioning of the sensory element to be maintained when the sensor comes into contact with the sample. In still other embodiments, one or more surfaces of the sensory element may be fixedly attached to a portion of the substrate such that the sensory element extends away from the substrate and is suspended from the point of attachment. Such embodiments include, but are not limited to, microcantilever devices.

The substrate of various embodiments may vary in thickness and composition. The skilled artisan will readily understand the physical characteristics required for a substrate such as, for example, thickness, shape, size, and composition, based on considerations such as, but not limited to, the intended use of the sensor. For example, in some embodiments, the substrate may make up a portion of a device or a housing for such device. As such, the substrate may be of sufficient thickness to maintain the structural integrity of the device. In other embodiments, the substrate may be a platform, wafer or chip that is removably inserted into a device. Thus, the substrate may be relatively thin, but of sufficient thickness to maintain and stabilize the sensory element in the device during use. Accordingly, the thickness of the substrate may vary from, for example, less than 1 μm to up to about several centimeters.

In some embodiments, the functional component may be deposited directly onto the substrate to create the sensory element that is integral with the substrate. In other embodiments, the sensory element may be separate from the substrate and may be removably placed in contact with the substrate either during manufacture of the sensor or prior to use of the sensor. In such embodiments, the sensory element may include a "base material" of a generally rigid substance that maintains the integrity of such sensory element. The base material may be any substance known in the art including, but not limited to, polymers, copolymers, silicon-based compounds, glass, metals, metallic compounds, metal alloys, composites, and combinations thereof. In some embodiments, the base material of the sensory element may be, for example, silicon, silicon nitride, or silicon oxide. In certain embodiments, the base material may be a polished microcrystalline wafer of silicon or a silicon-on-insulator (SOI) substrate having, for example, a bottom layer of single-crystal silicon or silicon nitride, a middle layer of silicon oxide, and a top layer of single-crystal silicon or silicon nitride. In yet other embodiments, the base layer may include a polymeric material. A wide variety of polymeric materials are available such as, but not limited to, thermosets, thermoplastics or polymeric composites such as, for example, polymer and copolymer composites that include ceramic, metallic, inorganic or polymeric nanoparticles, carbon nanotubes and the like. The thickness of the base material may vary depending on factors such as, the type of material utilized, the use of the sensor, and/or the characteristics of the device in which the sensor is used. For example, in some embodiments, the base layer may be from about 10 nm to about 10 mm thick.

In some embodiments, the functional component may adhere directly to the base material of the sensory element. In other embodiments, the sensory element may include one or more additional layers or "coating" applied to at least a portion of one or more sides of the base material that facilitate binding of the functional component to the sensory element. The coating or coatings of embodiments of the invention can include any coatings known in the art. In some embodiments, the base material of the sensory element of certain embodiments may be coated on at least one side with a surface layer of, for example, metal, such as, gold, silver, platinum, copper, palladium, aluminum, titanium or mercury, metal oxide, such as silica, or polymer or copolymer or a combination thereof. Such coating may facilitate binding of the functional component to the sensory element. In still other embodiments, the sensory element may include one or more adhesive layers of, for example, chromium (Cr), titanium/chromium (Ti/Cr) or a polymeric adhesive, between the base material and surface layer, which may allow the surface layer to adhere to the base material of the sensory element.

Such coatings may be deposited onto the base material by any method known in the art, such as, dip or spin-coating, ink jetting, roll coating, screen coating, chemical vapor deposition or physical vapor deposition, to name a few. In some embodiments, these coatings may be applied in a pattern using direct-write deposition techniques such as, for example, photolithography and similar techniques. The thickness of such coatings may vary. For example, in certain embodiments, the adhesive layer may be from about 1 nm to about 2000 nm thick or about 2 nm to about 50 nm thick or about 2 nm to about 10 nm thick and the base material may be from about 10 nm to about 2000 nm or 50 nm to about 400 nm thick. In other embodiments, the thickness of the base material and/or any of the coatings may extend above or below the range recited above based on factors such as the materials utilized and the coverage required.

Sensors containing a functional component of embodiments of the invention may be designed and constructed using any method known in the art. For example, in some embodiments, the sensor utilizes a substrate in the form of a chip or wafer wherein polymerization and/or depolymerization of the functional component is detected using a detector configured to monitor, for example, a change in temperature, conductivity, refractive index or surface energy. In other embodiments, the sensor may be a cantilever-based sensor wherein polymerization and/or depolymerization is detected using a detector configured to monitor deflection of a microcantilever using, for example, an optical detector, an interferometer-type detector, a piezoelectric-type detector or a capacitive-type detector.

The functional component may be deposited on the sensory element by any method known in the art. For example, in some embodiments, the functional component may be deposited on the sensory element using spin-coating, dip coating, ink jetting, roll coating, screen coating, ink jet printing, microspray methods, chemical vapor deposition (CVD), initiated chemical vapor deposition (iCVD), oxidative chemical vapor deposition (oCVD) or patterned using photolithography. Detailed information regarding CVD, iCVD, and oCVD can be found in "Initiated and Oxidative Chemical Vapor Deposition of Polymeric Thin Films: iCVD and oCVD," *Adv. Funct. Mater.*, 9999, 1-14, (2008), which is hereby incorporated by reference in its entirety. The choice of the process for deposition on the sensory element is dependent upon the nature of the functional component being employed.

In particular embodiments, the functional component may include self-assembled monolayers (SAMs) chemically adsorbed onto the surface of the sensory element. The SAMs are capable of detecting a wide variety of analytes in both liquid and vapor environments and samples. In such embodiments, the functional component may include a "head group" having an affinity for the outermost surface of the sensory element. For example, functional components prepared for adhesion to a sensory element having a metallic surface layer may have an alkanethiol or disulfide-containing head group. In addition, functional components prepared for adhesion to sensory elements having a silicon surface layer may have an alkoxysilane or oxysilane-containing head group. Particular compounds that may be useful in embodiments in which the functional component is deposited on the sensory element as SAMs include, but are not limited to 11-mercapto-1-undecanol, 2-methyl acrylic acid 3-(hydroxyl-dimethyl-silanyl)-propyl ester, 2-methyl acrylic acid 3-(trihydroxyl-silanyl)-propyl ester, and the like.

SAMs may be deposited on one or more surfaces of the sensory element, in some embodiments, by immersing the sensory element in a solution containing functionalized SAMs, which may adsorb to the sensory element or the surface layer of such sensory element within from about 5 minutes to about 24 hours at room temperature. Deposition of SAMs on surfaces of sensory elements is known in the art and detailed information can be found in "Self-Assembled Monolayers of Thiolates on Metals as a Form of Nanotechnology," *Chem. Rev.*, 105, 1103-1169, (2005), the entirety of which is hereby incorporated by reference.

The functional component may be deposited onto a sensory element or surface layer of the sensory element at a density that allows for efficient polymerization or crosslinking of neighboring molecules. For example, in some embodiments, the functional component may be present at an areal density from about $10^{10}$ cm$^{-2}$ and about $10^{20}$ cm$^{-2}$ or about $10^{12}$ cm$^{-2}$ and about $10^{16}$ cm$^{-2}$. Without wishing to be bound by theory, a self-amplified response elicited by a free radical initiator may intensify with increased mobility of reactive groups. Therefore, the density with which the functional component is disposed on the sensory element may affect the sensitivity of the device because, for example, an increased distance between neighboring molecules may reduce the likelihood of a reaction occurring between such reactive groups or high density deposition may restrict the movement of the reactive groups. In addition, functional components having shorter aliphatic chains linking the reactive group to the head group may exhibit reduced mobility, which may in turn reduce the likelihood of a reaction occurring between reactive groups of neighboring molecules. Therefore, functional components having shorter aliphatic chains may be deposited in higher density to achieve optimal mobility. Alternatively, functional components with a relatively higher number of carbons in the aliphatic chain may be utilized to enhance mobility of the reactive groups. In still other embodiments, combinations of SAMs having different mobility characteristics may be deposited on a sensory element to achieve optimal responsiveness from the sensory element.

The functional component of embodiments of the invention may be used in any type of sensor. For example, some embodiments are directed to microcantilever-type sensors having a functional component deposited on at least one side of the microcantilever sensory element. Microcantilever sensors are well known in the art, see, e.g., "Microcantilevers: Sensing Chemical Interactions via Mechanical Motion," *Chem. Rev.*, 108, 522-542, (2008), hereby incorporated by reference in its entirety. Any microcantilever device or micrometer-sized mechanical structure known in the art such as, but not limited to, micro-cantilevers, micro-bridges and micro-membranes may be modified to include embodiments of the invention. In one embodiment, the sensor may be a commercially available microcantilever chip or wafer having silicon-based microcantilevers each coated with gold on one side, and a layer of functional component, such as, for example, methacrylate functionalized 11-mercapto-1-undecanol deposited onto the microcantilevers to create a microcantilever sensor. In other exemplary embodiments, a commercially available chip or wafer including silicon-based microcantilevers may be coated on one side with an alkoxysilane containing a functional component having methacrylate functional groups to create a microcantilever sensor that can detect free radicals. In such embodiments, the functional component begins a self-amplified polymerization when contacted by a free radical or other polymerization inducing substance or energy, which may cause a deflection of the microcantilever sensory element detectable by any conventional means such as, for example, piezoresistance.

In other embodiments, functional components, such as, but not limited to, methacrylate functionalized mercapto terminated polymers and alkoxysilane-containing compounds including methacrylate functional groups may be deposited onto a commercially available chip or wafer composed of, for example, silicon, silicon nitride, SOI, glass, metal, metal coated silicon, polymers, copolymers and the like. The functional components begin self-amplified polymerization when contacted by a free radical or other polymerization inducing substance or energy, which may cause a deflection of the microcantilever sensory element that can be detected by any conventional means such as, for example, Fourier transform infrared (FTIR) spectroscopy.

The size and shape of sensory elements may vary throughout embodiments of the invention and may depend on the type and use of the sensor. In some embodiments, the sensory element may be a chip or wafer having a size and shape consistent with those known in the art. For example, a sensory element that is configured as a chip or wafer may be square or rectangle having a length and/or width of from about 100 μm to about 100 nm, or a circle having a similar surface area. In other embodiments, the sensory element may be a beam or a T-shaped sensory element utilized in microcantilever devices. For instance, in embodiments wherein the sensory element is utilized in a microcantilever device, the beam may be from about 100 μm to about 750 μm long and about 10 μm to about 50 μm wide.

Embodiments of the invention are also directed to methods for preparing a sensor including a functional component. For example, methods embodied by the invention may include the steps of providing a sensory element such as a chip, wafer or microcantilever, and depositing a functional component including a polymer or molecular compound including at least a functional group or head group for adhering to at least one surface of the sensory element and a linker for connecting the functional group or head group to at least one reactive group or intermediate group that can be chemically functionalized into a reactive group. In some embodiments, the reactive group may be joined to the linker during the deposition step. For example, in one embodiment, the functional component may include mercapto or alkoxysilane head groups and a linker including an alkyl chain of 2-20 carbons and a methacrylate reactive group. In others, the functional component deposited on the sensory element may be a precursor having a non-reactive intermediate group that may be replaced or modified to form a reactive group in one or more subsequent or additional steps. For example, in one embodiment, a precursor polymer including a mercapto or alkoxysilane functional or head group and a hydroxyl-terminated linker including an alkyl chain of 2-20 carbon atoms may be deposited onto the sensory element. The precursor polymer containing sensory element may then be treated with, for example, methacrylol chloride, which may react with the hydroxyl group of the precursor polymer to form a methacylate reactive group on the precursor polymer. Other intermediate groups could include amines and carboxylic acids, to name a few. Reactive groups could include, but are not limited to, acrylates, substituted acrylates, vinyls, alkenes, alkynes and the like.

Embodiments of the invention are also directed to methods for using a sensor including a functional component to detect peroxides. The methods of such embodiments may include the steps of heating a sample to a temperature sufficient to cleave peroxide-containing compounds to form a peroxide radical such as, for example, about 150° C. to about 300° C., and contacting a sensor including a functional component with the heated sample. Polymerization of the functional component triggered by interaction with the peroxide radical may be detected using any conventional method known in the art. For example, in one embodiment, the sensor may be a chip or wafer having a coating of a functional component including a polymer having a mercapto or alkoxysilane functional or head group bound to a surface of the chip, a linker including an alkyl chain of 2-20 carbons, and a methacrylate reactive group attached to the linker. An air, vapor, liquid or water sample heated to about 200° C. may be passed over the chip. The heat source embodied in the invention may include any heat source known in the art. In certain embodiments of the invention, heating of the sample can occur using an array of one or more filaments or any other resistively or otherwise heated element known in the art. The chip may be monitored for polymerization using any of the detection methods described above, for example, FTIR. In another embodiment, the sensor may be a microcantilever-type sensor having a microcantilever sensory element that is coated with a functional component including a polymer having a mercapto or alkoxysilane functional or head group bound to a surface of the microcantilever sensory element, a linker including an alkyl chain of 2-20 carbons, and a methacrylate reactive group attached to the linker. An air, vapor, liquid or water sample may be heated to about 200° C. and passed over at least the microcantilever sensory element. Cantilever response of the microcantilever sensory element may be monitored while the heated sample is passed over the sensor using any method known in the art such as, for example, monitoring piezoresistance.

Embodiments of the invention are further directed to devices for detecting peroxides, and such devices may be used to detect peroxides in any state, e.g., gas, liquid or solid. In certain embodiments of the invention, an apparatus for detecting the presence of peroxides is provided that includes a reactor comprising at least one chamber, at least one vapor entry opening wherein vapor enters the reactor and at least one vapor exit opening wherein vapor exits the reactor, a heat source positioned to heat vapors within the reactor, and one or more sensors. The sensors include one or more sensing elements having at least an upper and a lower surface wherein at least one surface is coated with a functional component having reactive groups, the reactive groups being capable of reversibly crosslinking when contacted by at least one free radical. In certain embodiments, the sensors may be positioned to receive the heated vapor. In certain aspects of the invention, the heat source may include an array of one or more filaments. In other aspects, the heat source may include a resistively or otherwise heated element.

Figure 3:
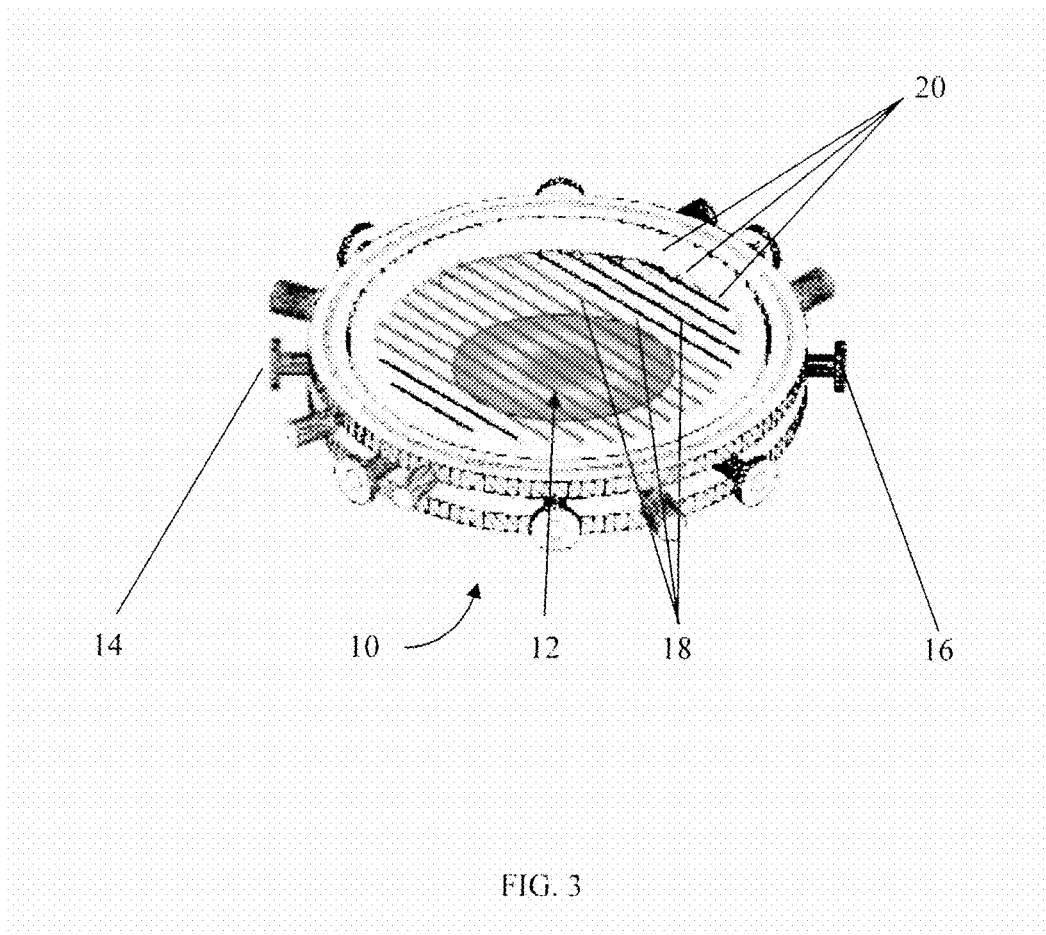
FIG. 3 is a schematic of a device of one embodiment of the invention for detecting free radical forming compounds using sensors with a functional component.

For example, in some embodiments, as illustrated in FIG. 3, such an apparatus may include a reactor 10 having at least one internal chamber 12, at least one entry opening 14 where a sample enters the chamber 12 and at least one exit opening 16 where the sample exits the chamber 12. A heating element, such as, for example, a plurality of filaments 18, for heating the sample may be positioned within the chamber 12 to heat the sample to a temperature sufficient to cleave a peroxide of peroxide-containing compounds. One or more sensors including a functional component 20 may be provided within the chamber 12 and positioned to come in contact with the sample following heating. One or more detectors for monitoring the polymerization state of the functional component may be provided within the chamber as well or may comprise an integral part of the sensor.

The reactor may be any type of reactor known in the art and can be configured in any way. For example, in some embodiments, the reactor may house a single chamber wherein the sample is heated and peroxides are detected. In other embodiments, the reactor may contain more than one chamber. For instance, a reactor may include a first chamber to heat the sample and a separate second chamber to detect peroxides from the heated sample. In still other embodiments, the reactor may further include additional chambers such as, but not limited to, a holding chamber wherein the sample is collected or a concentrating chamber wherein peroxides or peroxide-containing compounds are concentrated from a sample prior to detection. The chambers of multi-chamber embodiments of the reactor may be connected using any means known in the art. For example, separate chambers may be connected with tubes or hoses or consecutive chambers within the reactor may be conjoined such that a portal exists between each chamber that separates one chamber from the next. The entry opening and exit opening as well as connections between chambers may further include any number of valves and various secondary sensors, such as, for example, sensors for monitoring temperature, pressure, air flow and so on, which may be used to ensure proper function of the device and/or to optimize detection. The single and multi-chamber reactors in embodiments of the invention may be prepared from any type of material known in the art including, for example, thermosets, thermoplastics, composites, carbon fiber, metal, metal alloys, and combinations thereof.

The heating element of embodiments of the invention may be any type of heating element known in the art. In some embodiments, the heating element may be a plurality of resistively heated filaments positioned within the chamber. In other embodiments, the heating element is positioned on a surface of the chamber and provides heat to such surface thereby heating the contents of the chamber. In still other embodiments, heating elements may be positioned in portals or connectors between chambers and/or at the entry opening and/or exit opening of the reactor. In addition, combinations of heating elements may be used. For example, a filament type heating element may be used in combination with chamber surface heating elements to heat the sample.

Sensors including a functional component may be positioned at any location within the reactor such that a stream of sample is able to pass over the sensor while the device is in use. For example, in some embodiments, the sensors may be positioned on one or more internal surface of the reactor, and in other embodiments, sensors may be positioned on every internal surface of the reactor. In certain embodiments, sensors may be positioned such that they may be easily replaced. In such embodiments, the reactor may include one or more entry hatches that allow access to the internal chamber of the reactor such that the chamber and/or sensors may be maintained or sensors can be replaced. The sensors may be exposed when such a hatch is removed, or sensors may be positioned on the hatch such that they may be removed from the chamber of the reactor when the hatch is removed or opened.

In some embodiments, the sample may be allowed to flow into and out of the reactor through, for example, diffusion, gravity, thermal gradients, or volume expansion/compression resulting from phase changes of the sample. In other embodiments, the sample may be mechanically forced through the reactor. For instance, devices of certain embodiments may also include a means for providing a flow of sample through the chamber. In some such embodiments, a fan or turbine may be utilized to generate a flow of ambient air sample through the chamber. The fan or turbine may be positioned near the entry opening to force such air sample into the chamber, or the fan or turbine may be positioned near the exit opening to pull the air sample through the chamber. In other embodiments, a fan or turbine may be positioned at both the entry opening and the exit opening, and in embodiments in which the reactor contains more than one chamber, separate fans or turbines may be positioned between such chambers.

The sensing devices of various embodiments may be hand held, stand alone or walk-through. For example, in some embodiments, one or more sensing devices may be contained within a housing fashioned to provide, for example, a handle or include a separate handle to provide a hand held device. In such embodiments, the device may be of a particular size and weight such that an individual user may easily transport and use the device. In other embodiments, a device incorporating one or more peroxide sensors may be fashioned into a wall mounted device that may be positioned to continually monitor an area where peroxide-containing compounds are used or stored such as, for example, a chemical laboratory or storage facility, or integrated into a vehicle that uses peroxide-based fuels, and trigger an alarm when peroxide-containing compounds or a concentration of peroxide-containing compounds higher than a threshold amount are detected. In still other embodiments, one or more sensing devices may be fabricated into a portal for humans, cargo, baggage and the like, and may be used, for example, in airport security in a manner similar to metal detectors and sniffer-type devices currently utilized. In such embodiments, a walk-through housing may hold any number of additional devices in combination with the peroxide sensors of embodiments of the invention such as, for example, other chemical detectors, metal detectors, radiation detectors, CT-scanners, X-ray machines, cameras and the like. These additional complementary devices can be integrated into the same housing or sensing device, or installed in separate housings or devices.

In some embodiments, a peroxide detecting device may be provided as an auxiliary component capable of being added to a preexisting device. For example, walk-through devices used to detect explosives, metal or radiation may be fit with one or more auxiliary components including peroxide detection devices of embodiments of the invention. In particular embodiments, sniffer-type walk-through detectors that detect trace amounts of contaminants associated with bomb manufacture and handling by passing air over an individual positioned therein, may be fit with an auxiliary component that detects peroxides from the air stream created by the device. In such embodiments, trace amounts of peroxide may be detected using devices embodied by the invention by detecting trace amounts of peroxide attached to an individual, or an individual's belongings, who has been in contact with such explosives or detecting small amounts of peroxide-containing compounds that are emitted by liquids used in the preparation of such explosives. For example, peroxide-containing compounds such as, triacetone triperoxide (TATP) and hexamethylene triperoxide diamine (HMTD) and their constituent components, including hydrogen peroxide, can be reliably detected using the devices of embodiments of the invention. The sensors, methods and devices of embodiments of the invention may be easily fabricated and used to detect such compounds.

In each of the devices embodied, any number of additional components may be provided. For example, the devices of the invention may include one or more of the following: controllers or buttons for controlling the operation of the device, audio or visual alarms, gauges, monitors, cameras, secondary devices for detecting other compounds or substances, fans or turbines and so on.

EXAMPLES

In order that the invention disclosed herein may be more efficiently understood, the following examples are provided. These examples are for illustrative purposes only and are not to be construed as limiting the invention in any manner.

Example 1

Methacrylate Functionalization on Gold Substrates

Figure 4:
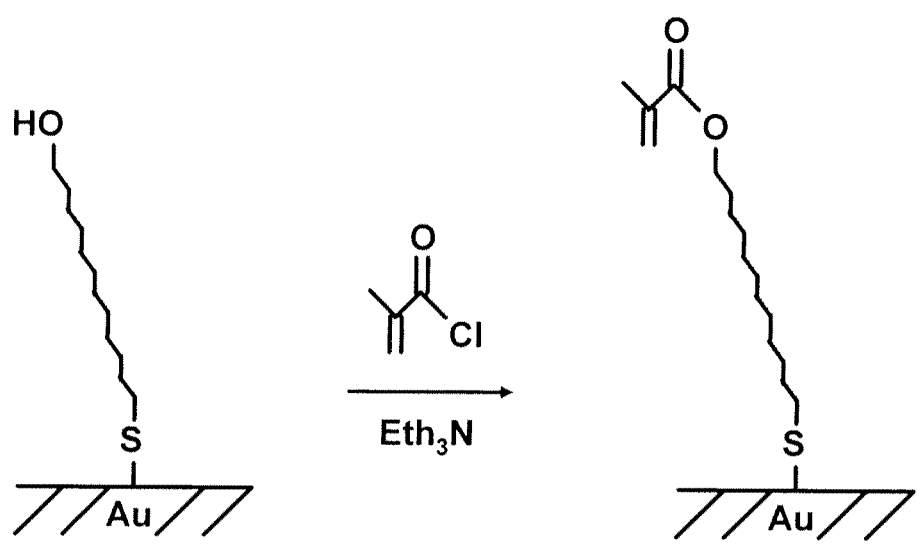
FIG. 4 illustrates the formation of a functional component comprising methacrylate functionalized self-assembled monolayers (SAMs) on gold-coated substrates.

An exemplary procedure for forming a functional component comprising methacrylate-terminated self-assembled monolayers (SAMs) on a gold or gold-coated substrate or microcantilever sensory element is provided in FIG. 4. SAMs having a mercapto-containing head group and a hydroxyl-terminated end group were covalently attached to gold-coated substrates or microcantilevers by binding the mercapto-containing group to the gold surface using self-assembly mechanisms. The hydroxyl end groups were subsequently substituted with methacrylate end groups.

In this example, evaporated gold coatings having a thickness of 2500 Å on silicon with titanium (Ti) or titanium/chromium (Ti/Cr) adhesion layers were utilized because chips, wafers or microcantilevers comprising such materials provide an ultra-smooth surface, thereby minimizing SAM defects. The gold-coated test substrates or microcantilevers were cleaned and activated using plasma treatment prior to use. Specifically, a Harrick Plasma chamber was used to activate gold-coated microcantilevers or test substrates with oxygen plasma immediately or soon prior to self-assembly of the SAMs. The chamber was purged five times with nitrogen (99.999%) from a base pressure of 60 mTorr. Oxygen (99.99%) was then fed to the chamber at 1 slm with the chamber pressure controlled at 300 mTorr. Plasma was then applied at "High" for 5 min. The gold-coated microcantilevers or test substrates were then immediately immersed in pure ethanol for 20 minutes following the plasma treatment to wash away residues and mitigate oxidation of the gold-coated surfaces.

To achieve assembly of SAMs, the plasma treated gold-coated surfaces were immersed in a 2 mM solution of 11-mercapto-1-undecanol in ethanol for 24 hours, which resulted in densely packed SAMs. The resulting hydroxyl end groups were then converted to methacrylate-terminated SAMs by treating the dried surfaces of the microcantilevers or test substrates with a 0.2 M tetrahydrofuran (THF) solution of methacryloyl chloride including a slight excess of triethylamine to trap hydrochloric acid (HCl) generated by the substitution reaction. At a concentration of 0.2 M, the methacryloyl chloride was in strong excess, relative to SAM areal density on the order of $10^{14}$ cm$^{-2}$. To ensure that the reaction was carried out in the absence of water (to avoid unwanted reaction with water), all glassware was cleaned and dried at 110° C. for 8 hours, and the reaction was carried out in a 3-headed flask under nitrogen. The methacrylol treated samples were then rinsed in THF and dried.

Figure 5:
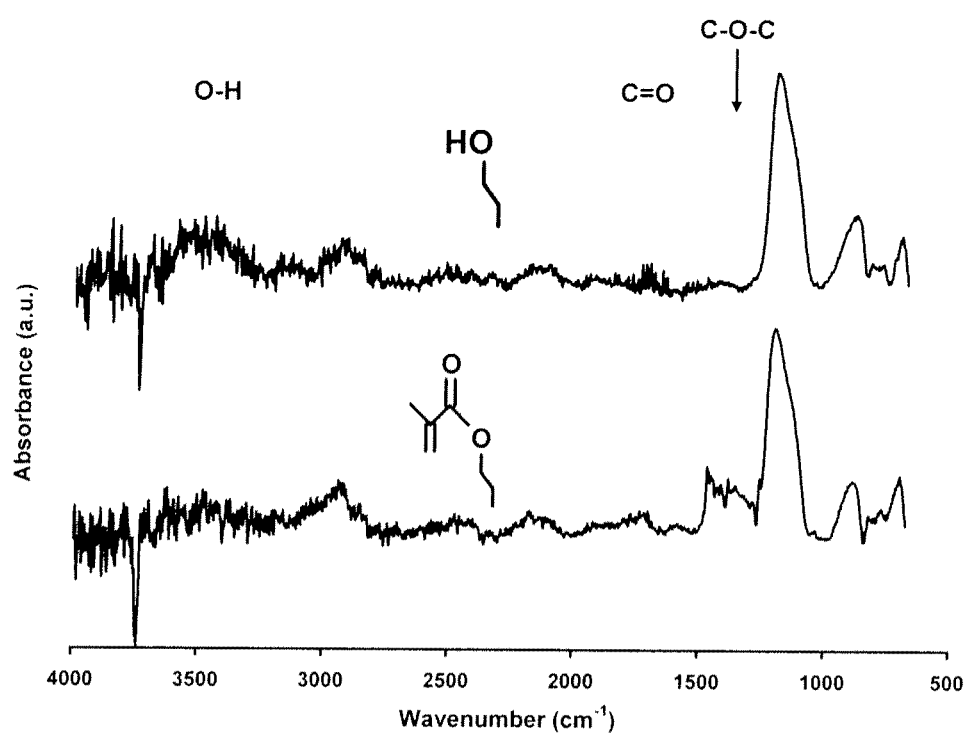
FIG. 5 is a grazing angle Fourier transform infrared (FTIR) spectrograph illustrating the self-assembly of hydroxyl terminated self-assembled monolayers (SAMs) on a gold-coated substrate and subsequent conversion of the hydroxyls to methacrylate reactive groups.

To verify the self-assembly of the 11-mercapto-1-undecanol on gold-coated substrates and the subsequent conversion of the hydroxyl end groups to methacrylate, grazing angle Fourier transform infrared (FTIR) spectroscopy was performed. FIG. 5 shows the results of the grazing angle FTIR, the —OH moiety of the SAM precursor is clearly visible at 3500 cm$^{-1}$. After treatment of the SAM with methacryloyl chloride, the —OH peak diminishes, and a new peak corresponding to C—O—C is apparent. A stronger indication of the carbonyl (C=O) presence in the methacrylate end group is also apparent. Sensitivity of the methacrylate-terminated SAMs to peroxide radicals was confirmed with direct measurements of functionalized microcantilevers using atomic force microscopy (AFM) optics as described below.

Example 2

Methacrylate Functionalization on Silicon Substrates

Figure 6:
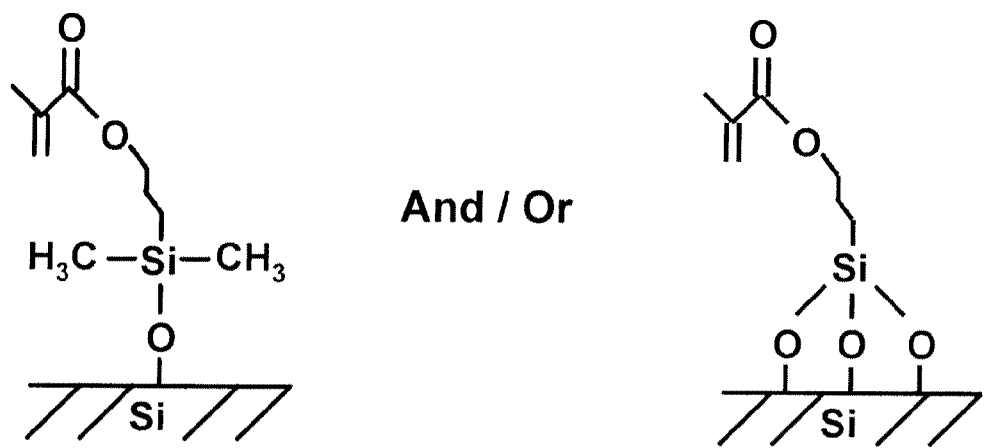
FIG. 6 illustrates formation of a functional component comprising self assembly of silane-containing compounds (Si SAM I and Si SAM III) on a silicon substrate.

FIG. 6 shows the general scheme utilized for methacrylate functionalization of sensory elements comprising silicon surfaces. SAMs formation on silicon with alkoxysilanes is well-established and several alkoxysilane precursors that include methacrylate end groups are commercially available. Methacryloxypropyldimethylmethoxysilane (95%) (Si SAM I), and methacryloxypropyltrimethoxysilane (Si SAM III) were utilized for the purposes of this example.

Functionalization of silicon with a methacrylate-terminated SAM was achieved by immersing activated silicon substrates into a 2 wt % solution of Si SAM I or Si SAM III in 95% ethanol/5% water for approximately 12 hours. Drops of acetic acid were added throughout incubation to adjust the pH of the solution to 4.5-5.5. The treated samples were rinsed in ethanol and dried at 110° C. for at least 10 minutes. Self assembly onto the silicon substrates occurred within minutes in the ethanol/water solvent system.

Samples produced from Si SAM I and Si SAM III precursors were compared to assess the affect of individual vs. multiple points of attachment to the silicon surfaces. Si SAM I provided the more ordered monolayer relative to Si SAM III because the three active sites on Si SAM III enable crosslinked pathways, which may lead to amorphous multilayer buildup. In addition, because a self-amplified response to peroxide radical initiators intensifies with increased mobility of the end groups, the functionalized silicon surfaces using polymers having only a 3 carbon chain may be less sensitive to peroxide targets than those having a 12 carbon chain, such as 11-mercapto-1-undecanol. Precise surface morphology may be tunable using mixtures of Si SAM I and Si SAM III.

Example 3

SAMs/Gold-Coated Microcantilever Sensing Device

Figure 7A:
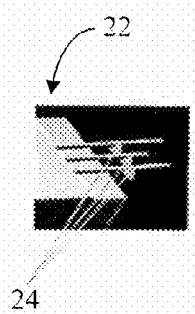
FIG. 7A is a functionalized microcantilever substrate sensing device of one embodiment of the invention.
Figure 7B:
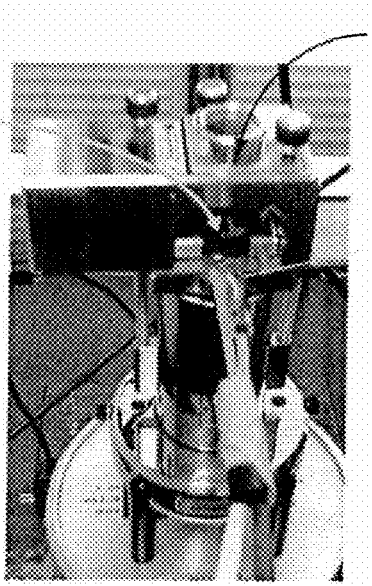
FIG. 7B is the microcantilever substrate of FIG. 7A mounted in a multi-mode atomic force microscope (AFM)
Figure 7C:
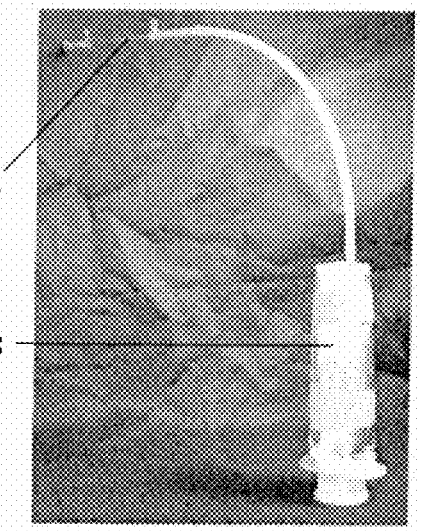
FIG. 7C shows attachments for peroxide sensitivity testing of the microcantilever substrate of FIG. 7A mounted in a multi-mode atomic force microscope (AFM) shown in FIG. 7B.

Tipless microcantilevers of bare silicon or gold-coated silicon are commercially available and are provided on a chip 22 having six microcantilevers 24 per chip with three microcantilevers 24 on each end, as illustrated in FIG. 7A. Following methacrylate functionalization, the microcantilevers 24 were mounted onto a Veeco Multi-Mode Atomic Force Microscope (AFM) 26 and a syringe 28, connected to a heated filament 30, was used to deliver vapor samples to the vicinity of the chip 22. See FIGS. 7B and 7C.

Figure 8:
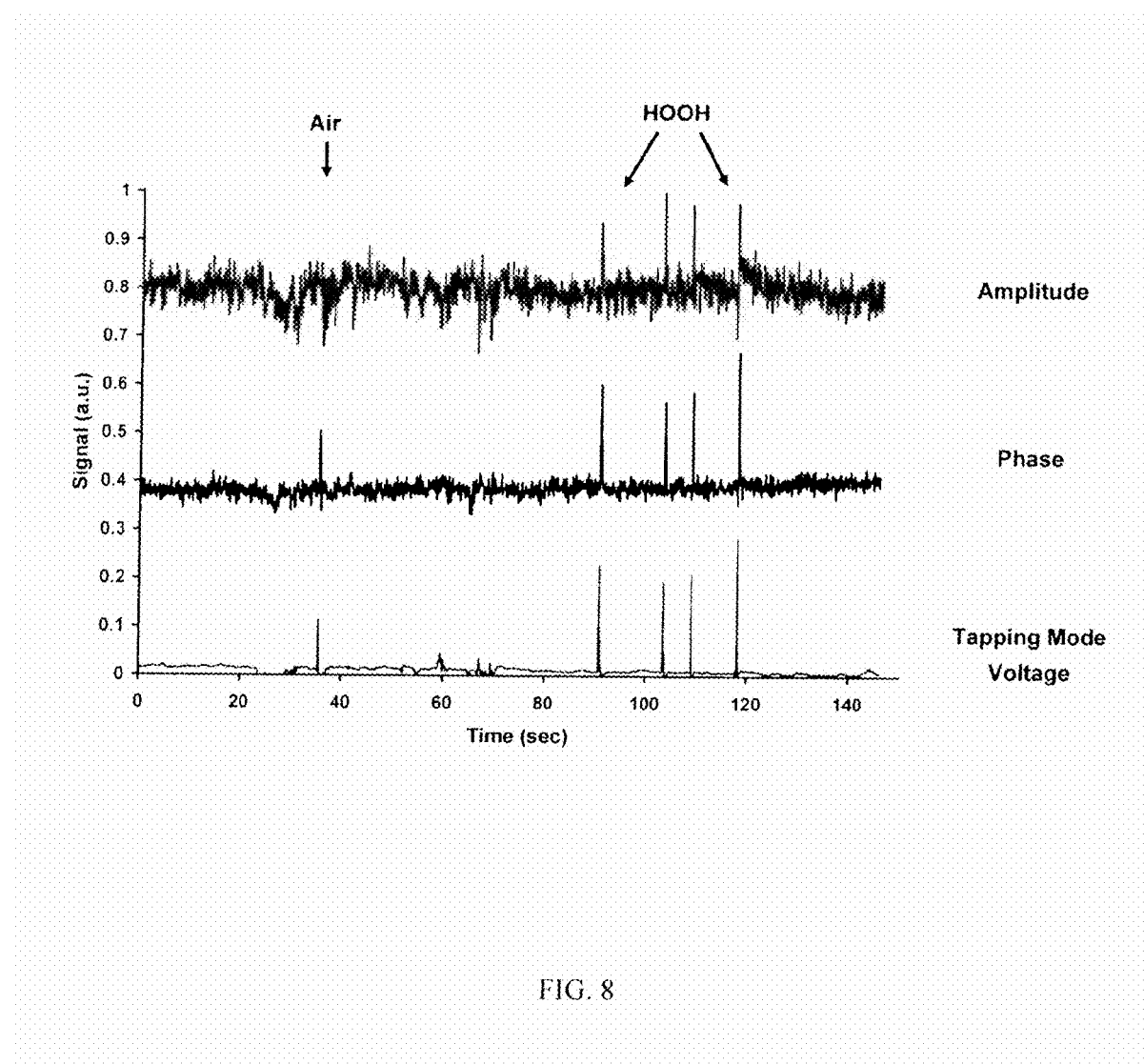
FIG. 8 shows the response of a microcantilever substrate without a functional component including self-assembled monolayers (SAMs) exposed to air blanks and peroxide radicals as measured using atomic force microscopy (AFM)
Figure 9:
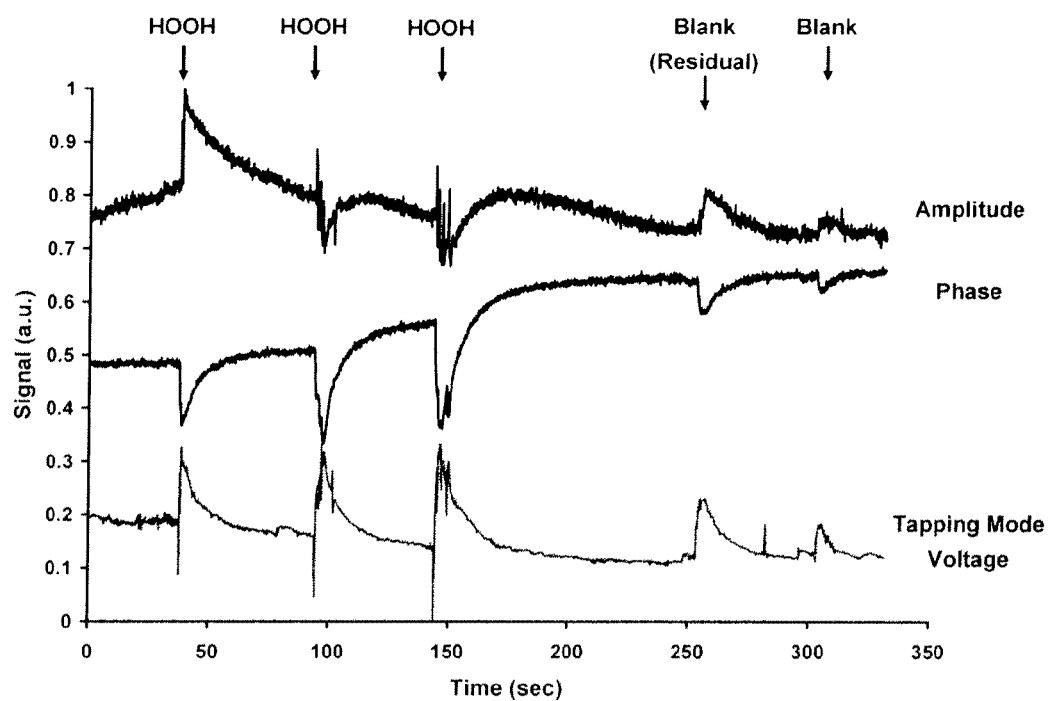
FIG. 9 shows the response of functionalized self-assembled monolayers (SAMs) on a gold-coated microcantilever substrate sensory element exposed to peroxide radicals followed by air blanks as measured using atomic force microscopy (AFM)
Figure 10:
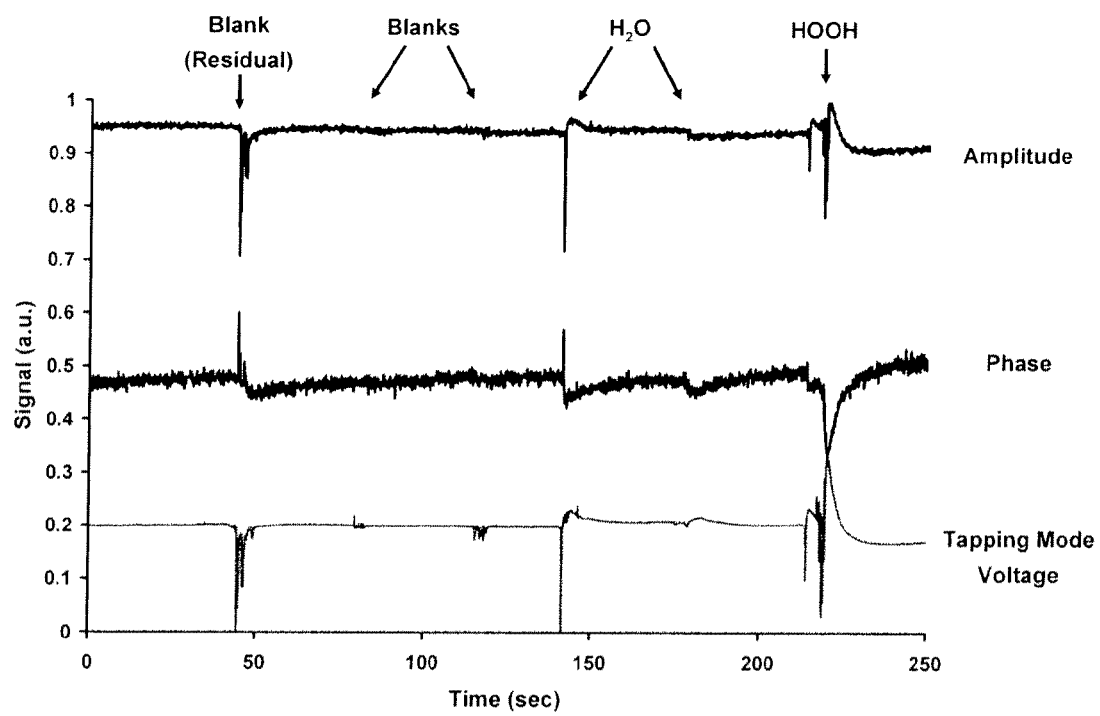
FIG. 10 shows response testing of functionalized self-assembled monolayers (SAMs) on a gold-coated microcantilever substrate sensory element as measured using atomic force microscopy (AFM)

A typical cantilever response characterized using AFM from a blank, non-functionalized microcantilever is shown in FIG. 8. The spikes correspond to air movement caused by the vapor samples as they arrive, and the amplitude appears to depend on the force of the syringe. In comparison, the peaks corresponding to cantilever responses to peroxides by functionalized gold-coated microcantilevers are broader, as illustrated in FIG. 9 and FIG. 10. The slightly broadened peaks from blank air bursts shown in FIG. 9 are likely due to residual hydrogen peroxide in the tubing, which is evidenced by the second air burst providing a smaller peak that corresponds to the lines being purged of residual peroxide. FIG. 10 depicts a difference between the sharp responses from blank air samples and the broader response from peroxide. FIG. 10 also shows a test on the second cantilever to water, a key interferent for peroxide systems. No broadened signal was observed for water relative to peroxides.

Example 4

SAMs/Silicon Microcantilever Sensing Device

Figure 11:
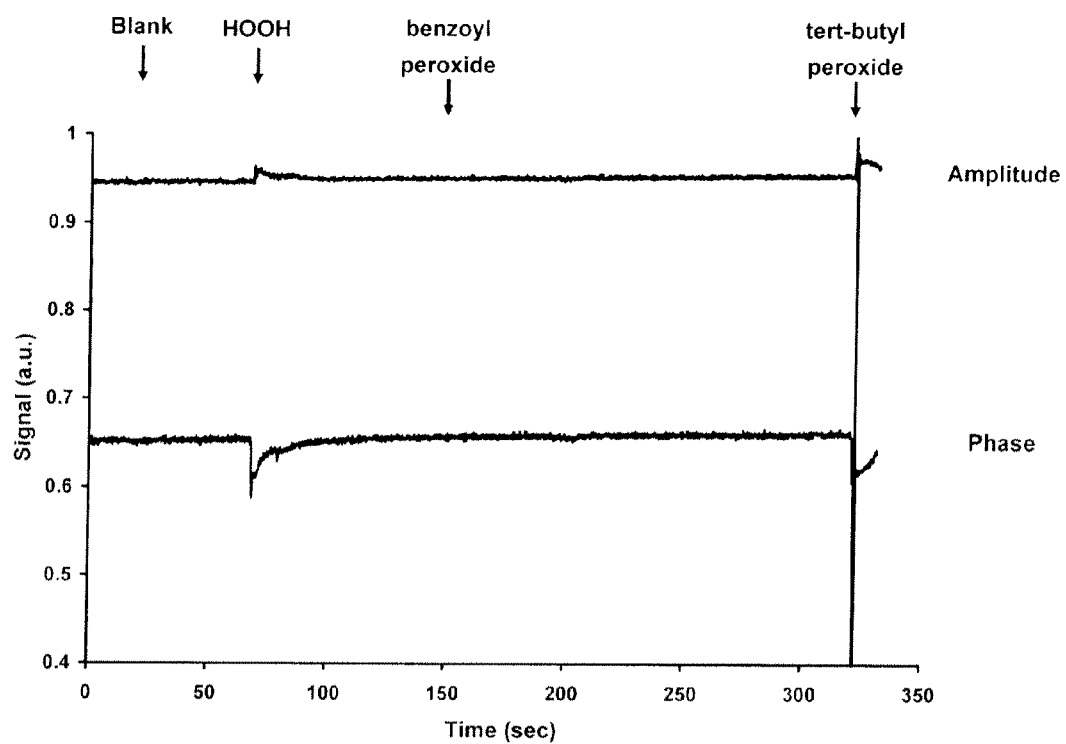
FIG. 11 shows response testing of a silicon microcantilever substrate functionalized with Si SAM I as measured using atomic force microscopy (AFM)

FIG. 11 illustrates the responsivity of a silicon microcantilever functionalized with Si SAM I to peroxides as measured using AFM. No cantilever response was observed for benzoyl peroxide, which may be due in part to low vapor pressure, benzoyl radicals having short lifetimes relative to hydrogen and tert-butyl peroxide radicals, and deactivation in the gap between the heated filaments and the mounted cantilever. It is expected that benzoyl peroxide sensitivity will be enhanced once a test platform has been built to accommodate a heated filament installed very near the cantilevers, and also with the use of higher vapor-generating temperatures on the sampling end. Tert-butyl peroxide, the most stable of the peroxide radicals tested, generated the largest response and was the most difficult to purge from the tubing.

Figure 12:
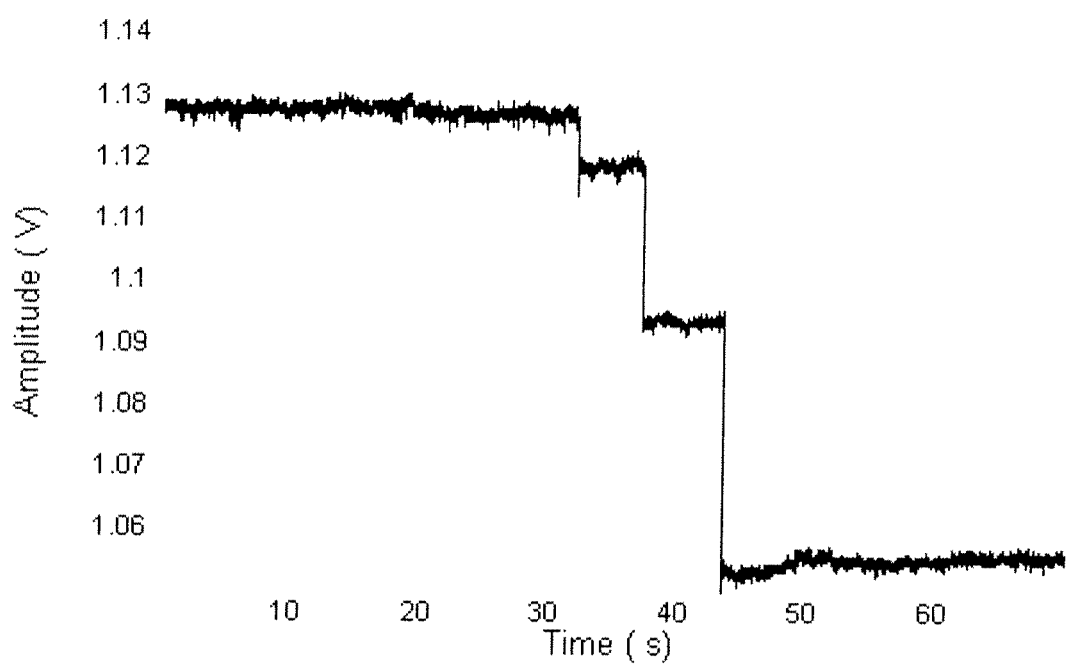
FIG. 12 shows a sample response curve for an irreversibly functionalized sensor as measured using atomic force microscopy (AFM).

The microcantilever responses to peroxide radicals appear to be reversible as shown in FIG. 9, FIG. 10, and FIG. 11, indicating the possibility of a self-unzipping mechanism. For comparison, FIG. 12 shows an exemplary response curve for an unrelated microcantilever sensor that does not exhibit such reversible behavior. Few degrees of freedom for the reactive tethered end groups is one explanation for this behavior. The minimum neighbor-to-neighbor distance for a fully dense SAM is about 1 nm, considering that there are $10^{14}$ end groups/cm$^2$. Without wishing to be bound by theory, this limitation in reaction partners makes termination of a growing live polymer chain less favored than in a system with full translational freedom, which may lead to self-unzipping.

What is claimed is:
1. A sensor for detecting reaction initiators comprising:
 a functional component comprising a plurality of reversibly polymerizable reactive groups, wherein said reactive groups exhibit a change in state of polymerization when contacted by free radicals;
 a sensing element comprising an upper surface and a lower surface, wherein at least one said surface is coated with a self-assembled monolayer of the functional component; and
 at least one detector fixedly attached to the sensing element, wherein the detector is capable of detecting the state of polymerization of the reactive groups of the functional component using a change in capacitance of the sensing element caused by polymerization of the functional component.
2. The sensor of claim 1, wherein the sensing element comprises one or more cantilever arms capable of reacting to the state of polymerization of the reactive groups.
3. The sensor of claim 2, wherein the one or more cantilever arms undergo a cantilever response when reacting to the state of polymerization of the reactive groups.
4. The sensor of claim 3, wherein the detector is capable of measuring the state of polymerization of the reactive groups by detecting a change in resistance, a change in natural frequency or a change in the Q-mode.
5. The sensor of claim 2, further comprising a piezoresistive element for detecting a mechanical parameter associated with the one or more cantilever arms.
6. The sensor of claim 5, wherein the piezoresistive element forms part of a balanced bridge.
7. The sensor of claim 6, wherein the balanced bridge is a wheatstone bridge.
8. The sensor of claim 1, wherein the detector is capable of measuring bending of the sensing element.
9. The sensor of claim 1, wherein the detector is capable of measuring a change in frequency associated with the sensing element.
10. The sensor of claim 1, wherein the at least one detector measures the state of polymerization by characterizing refractive index, charge change, torsion, temperature change, surface energy change, and combinations thereof of the functional component.
11. The sensor of claim 1, further comprising a substrate wherein the sensing element is fixedly attached to said substrate.
12. The sensor of claim 1, wherein the sensing element comprises a base material selected from a polymer, copolymer, silicon-based compound, glass, metal, metal alloy, composite material or combinations thereof.
13. The sensor of claim 12, wherein the base material is a silicon substrate.
14. The sensor of claim 13, further comprising a metallic coating on at least one surface of the silicon substrate.
15. The sensor of claim 1, further comprising an adhesive layer.
16. The sensor of claim 1, wherein the functional component comprises a head group selected from one or more of a mercapto group, an alkoxysilane having 1 to 3 oxygen atoms or a combination thereof for binding to the sensing element.
17. The sensor of claim 16, wherein the head group is utilized in self assembly of the functional component.

18. The sensor of claim 1, wherein the functional component comprises a substituted or unsubstituted, branched or unbranched, alkylene or alkenylene chain of 2 to about 20 carbon atoms.

19. The sensor of claim 1, wherein the reactive groups comprise acrylates, substituted acrylates, methacrylates, vinyls, alkenes, alkynes and derivatives and combinations thereof.

20. The sensor of claim 1, wherein the state of polymerization comprises crosslinking, uncrosslinking, polymerizing or depolymerizing that is innately reversible or regeneratably reversible.

21. The sensor of claim 1, wherein the free radicals are peroxide radicals, azo radicals, persulfate radicals or combinations thereof.

* * * * *